United States Patent [19]
Draenert

[11] Patent Number: 5,522,894
[45] Date of Patent: Jun. 4, 1996

[54] BONE REPLACEMENT MATERIAL MADE OF ABSORBABLE BEADS

[76] Inventor: Klaus Draenert, Gabriel-Max-Str. 3, 8 München 90, Germany

[21] Appl. No.: 39,517

[22] Filed: Mar. 29, 1993

Related U.S. Application Data

[63] Continuation of Ser. No. 935,647, Aug. 26, 1992, abandoned, which is a continuation of Ser. No. 651,104, Feb. 4, 1991, abandoned, which is a continuation of Ser. No. 528,347, May 22, 1990, abandoned, which is a continuation of Ser. No. 403,045, Aug. 31, 1989, abandoned, which is a continuation of Ser. No. 271,420, Nov. 10, 1988, abandoned, which is a continuation of Ser. No. 902,442, filed as PCT/EP85/00711, Dec. 16, 1985, published as WO86/03671 Jul. 3, 1986. abandoned.

[30] Foreign Application Priority Data

Dec. 14, 1984 [DE] Germany ............ 34 45 711.9

[51] Int. Cl.$^6$ ............................................. A61F 2/28
[52] U.S. Cl. .................. 623/16; 623/11; 623/66; 606/76; 433/201.1
[58] Field of Search .......... 106/75, 102; 427/2; 433/201.1; 623/11, 13, 16, 66; 606/66, 76, 77

[56] References Cited

U.S. PATENT DOCUMENTS

| | | | |
|---|---|---|---|
| 3,848,273 | 11/1974 | Frey | 623/22 X |
| 3,855,638 | 12/1974 | Pilliar | 623/16 |
| 4,051,598 | 10/1977 | Sneer | 623/16 |
| 4,177,524 | 12/1979 | Grell et al. | 623/16 |
| 4,192,021 | 3/1980 | Deibig et al. | 623/16 |
| 4,206,516 | 6/1980 | Pilliar . | |
| 4,230,455 | 10/1980 | Hidaka et al. | 433/202.1 |
| 4,347,234 | 8/1982 | Wahlig et al. | 623/16 |
| 4,365,357 | 12/1982 | Draenert | 128/92 C X |
| 4,373,217 | 2/1983 | Draenert | 623/16 |
| 4,542,539 | 9/1985 | Rowe, Jr. et al. | 623/16 |
| 4,544,359 | 10/1985 | Waknine | 433/202.1 X |
| 4,644,942 | 2/1987 | Sump | 623/16 |
| 4,655,777 | 4/1987 | Dunn et al. | 623/16 |
| 4,713,076 | 12/1987 | Draenert | 623/16 |
| 4,992,226 | 2/1991 | Piez et al. | 427/2 X |

FOREIGN PATENT DOCUMENTS

| | | |
|---|---|---|
| 0011809 | 11/1979 | European Pat. Off. . |
| 0016906 | 1/1980 | European Pat. Off. . |
| 8303967 | 11/1983 | European Pat. Off. . |
| 837294 | 4/1952 | Germany . |
| 2022498 | 5/1970 | Germany . |
| 2127843 | 6/1971 | Germany . |
| 2205808 | 2/1972 | Germany . |
| 2502884 | 1/1975 | Germany . |
| 2620809 | 5/1976 | Germany . |
| 2620907 | 5/1976 | Germany . |
| 611794 | 9/1976 | Germany . |
| 2730004 | 7/1977 | Germany . |
| 2742128 | 9/1977 | Germany . |
| 2854490 | 12/1978 | Germany . |
| 2917037 | 4/1979 | Germany . |
| 643732 | 6/1984 | Germany . |
| 1593288 | 7/1981 | United Kingdom . |
| 8303967 | 11/1983 | WIPO . |

*Primary Examiner*—Paul B. Prebilic
*Attorney, Agent, or Firm*—Kinney & Lange

[57] ABSTRACT

The invention relates to a bone replacement material consisting of a three-dimensional supporting framework of elementary bodies connected to one another and surrounding defined spaces, and a coating mass of fillers (based on strong calcium compounds) and a binding substance (matrix). The binding substance and the fillers are absorbable and the fillers are highly porous spherical particles with a diameter of between 15 and 50 μm and a pore volume of between 50 to 80%, to which some filamentous material can be added.

The bone replacement material of the invention is suited to produce coatings for prostheses, thus serving as an anchoring part for prostheses. It can also be used as a complete implant.

18 Claims, 6 Drawing Sheets

90

92

BONE REPLACEMENT MATERIAL MADE OF ABSORBABLE BEADS

This is a continuation of application Ser. No. 07/935,647, filed Aug. 26, 1992 (now abandoned); which was a continuation of application Ser. No. 07/651,104, filed on Feb. 4, 1991 (now abandoned); which was a continuation of application Ser. No. 07/528,347, filed on May 22, 1990 (now abandoned); which was a continuation of application Ser. No. 07/403,045, filed on Aug. 31, 1989 (now abandoned); which was a continuation of application Ser. No. 07/271,420, filed Nov. 10, 1988 (now abandoned); which was a continuation of application Ser. No. 06/902,442, filed as PCT/EP85/00711, Dec. 16, 1985, published as WO86/03671 Jul. 3, 1986.

BACKGROUND OF THE INVENTION

This invention relates to a bone replacement material and its use.

Attempts have always been made to fill bone gaps following bone injuries or surgical removal, since experience has shown that bone regeneration takes a long time and that an extremity's functioning is not restored until the bone has healed completely. It is hardly possible for large bone gaps to heal in such a way that the original function is restored. That is why attempts have been made for a very long time to use bone replacement materials, either as transplants or implants.

Unfortunately, the search for suitable materials has not been very effective. When using autologous material, i.e. from bone transplants from the same patient, the amount of material is limited since only certain parts of the locomotor system can be used to donate bone. Homologous material presents the problem of immune reactions—a problem which to date has not been solved. Although prepared homologous and heterologous bone material can be used to a limited extent for bone replacement, it is not fully accepted by the body and is not completely incorporated therein, as has been shown in experiments.

That is why attempts have been made to further treat animal bones and develop a bone replacement material capable of filling and bridging gaps. It has always been assumed that the bone's honeycomb structure should be maintained to the greatest possible extent.

All processes and all commercial materials, with the exception of the heterologous bone chips termed "cialit chips" or "Kiel chips", prepare animal bones or other collagens from animals in such a way that they are de-mineralized and lose their antigenicity through various chemical processes. The collagens obtained in this way are incorporated by the body and are also absorbable, but they are not suited for bearing biomechanical forces and do not serve as a stable supporting structure.

That is why attempts have been made again and again to develop materials with the properties of bone tissue, i.e. to provide support and to be absorbable. Various sintered tricalcium phosphates or apatites have been used primarily for this purpose. Attempts have also been made to facilitate the incorporation of total joint prostheses, for example, by structuring the surface of the implants. The incorporation of these prostheses can be compared to bone ingrowth in materials used for bone replacement implants. That is why similar demands are placed on the coating of a prosthesis, its structure and surface quality. To date, the problem of bone ingrowth and bone gap healing has not been solved in a satisfactory way. Bone replacement materials based on structured collagens, such as those proposed in DE-OS 28 54 490, do not exhibit a sufficient bone-building effect.

They indicate the structure the bone is to take, i.e. a trabecular structure, which only results in an inner and outer accumulation of reinforced and thickened trabeculae, but does not permit a normal bone architecture. In addition, due to de-mineralization, these materials no longer possess mechanical strength, thus explaining the lack in bone induction and excluding a supporting function. Sintered materials are hardly absorbable at all within a useful period of time.

The problems encountered in joint replacement are the same as those in bone replacement, plus the fact that the interface of a prosthesis is subjected to considerably more load than the interface of a bone replacement material. Prostheses, i.e. artificial joints, are generally anchored in the bone with a pin or stem (anchoring part) or are placed on the bone (see Journal of Bone and Joint Surgery, Vol. 21 (1939), pp. 269–288).

A common method of replacing a hip joint, for example, consists of inserting a full metal shaft into the bone marrow cavity and anchoring it there with a two-component plastic (bone cement) (J. Bone Joint Surg., Vol. 42B (1960), pp. 28–30). The known bone cements do not exhibit sufficient compatibility and biomechanical strength, however. During such procedures, it is generally necessary to enlarge the surface of the prosthetic stem. This is achieved, for example, by means of wave or saw tooth-like formations on the surface (see DE-PS 837 294). DE-OS 2 127 843 discloses a porous metal coating firmly connected with the base body of the same metal. Said coating is meant to enlarge the surface and permit bone ingrowth. Bone ingrowth only occurs under certain conditions with the known coatings. It is not possible to obtain reproducible results—transferrable to all patients—with such prosthetic surfaces. Thus, other factors play a role in ensuring bone ingrowth and anchoring for prognostic purposes.

In accordance with the invention, two main factors have been detected which induce the desired bone ingrowth and determine the morphology of a supporting or non-supporting bone structure and the related capability of bearing loads occurring without any difficulty. These are: 1. the morphology of the surface structure in the anchoring part and 2. the chemical composition (chemism) of its surface.

An experiment was conducted to determine the extent to which the individual bone-building cell, the osteoblast, and the osteoblast layer can be induced to build bone and specific trabeculae by means of different morphological and chemical structures and substances. A certain morphological structure in the anchoring part strongly induces bone formation by the bone-building cell, whereas a different morphological structure leads to the strongest formation of supporting trabeculae by the osteoblast layer. However, in order to achieve optimal static results, the required formations (topography) on the implant anchoring must be considered in the overall design. Moreover, the overall load and coordinated joint movement must also be taken into account with respect to prosthetic design which is decisive for the introduction of force.

Based on the above-mentioned findings and knowledge, in accordance with the invention, on bone induction and morphology as shaping criteria, four dimensions can be defined for the structuring of bone replacement materials. These shall be termed 1st to 4th order structures. On the basis of this definition, 1st order structure is the outer implant design, e.g. the shape of the prosthesis' anchoring part. The 2nd order structure represents the shaping of the surface (topography). Second order structure refers, for instance, to certain surface shapes such as a wave or saw tooth-like surface formation or a prosthetic stem with a step-like formation. The purpose of these 2nd order surface structures is to support mechanical anchoring and differentiate the anchoring surface with respect to load. In accordance with the present definition, 3rd order structure is the microstructure on the surface. This includes surface formations such as small spheres in the millimeter range. Finally, the 4th order structure refers to the ultrastructure with dimensions of approximately 20 µm.

DE-OS 27 30 004 teaches an anchoring part for total bone prostheses, in particular pegs, the surface of which presents a number of projections connected in one piece with the base body and separated from one another by spaces. It is characterized by the fact that the space separating two adjacent projections presents at least one narrow spot located at the level between the surface and the highest points of the projections.

The features of this known anchoring part range from the prosthetic design (1st order structure) to microstructure (3rd order structure), the latter being defined by the projections on the surface. The purpose of the projections is to permit improved cross-linking of the bone tissue in the spaces between the projections, and thus a more resistant anchoring of the bone tissue, preferably without a binding substance.

The surface formation of this known anchoring part does present a disadvantage, however: It does not present an optimal morphological structure and has no shaping elements for the bone-building cell and the supporting cortical bone. Moreover, the surface structures are not absorbable, not even in part. Therefore, the adhesion of the bone cell is to the base body is not as good as in absorbable surfaces. In addition, the bioactive and chemotactic effect (bone induction) is not as great in non-absorbable surface coatings as in absorbable coatings, especially if active substances are admixed to the latter. Finally, the microstructure on the surface of the anchoring part known from DE-OS 27 30 004 cannot take on admixtures such as hemostatic agents, bone-building substances, antibiotics, vaso-active substances and bone-active hormones.

The greatest disadvantage is the fact that the surface structure does not permit the formation of continuous supporting arched constructions.

DE-OS 26 20 907 describes a prosthetic stem coating of absorbable ceramic materials (calcium phosphate-based) and non-absorbable plastics. When the ceramic is absorbed, a continuous porous plastic structure is formed with bioactivating ceramic remainders on the pores' inner surfaces.

A non-absorbable plastic matrix presents a disadvantage, however: The plastic is pulverized by the shearing forces occurring in the interface and the wear material cannot be absorbed. This results in inflammations and can cause the prosthesis to loosen. Another major drawback in the coating described in DE-OS 26 20 907 is the fact that the absorbable ceramic particles soak up the non-absorbable plastic, thus resulting in a further reduction in the coating's overall absorbing capacity. For this reason, the bone surrounding the prosthetic anchoring cannot grow deeply and quickly enough to the base body (support). This causes a reduction in strength.

A surface structuring of the anchoring part of a stem prosthesis is known from U.S. Pat. No. 3,855,638. A 100 to 1,000 µm thick porous metal coating is applied to the substrate of the same metal. This coating consists primarily of spherical metal particles 50 to 150 µm in size with 20 to 200 µm large pores distributed in between. The dimensions and distribution of the spherical forming elements described in U.S. Pat. No. 3,855,638 as well as U.S. Pat. No. 4,206,516 are not very effective, however.

The forming element for the bone-building cell is less than 50 µm and preferably 15–30 µm in size. The forming element for the supporting trabeculae is between 580 and 1,000 µm. The size distribution of the non-absorbable formative elements in the coating described in the U.S. patents does not permit a rapid and long-lasting bone anchoring. As indicated in the patents, the spaces permit an ingrowth of filamentous structures and even woven bones, but not an ingrowth and penetration of the mature, supporting bone structures required for larger spaces.

The problem of the invention is to create a bone replacement material suited for the coating and surface structuring of bone implants and for use as a shaped complete implant. It must be penetrated deeply and quickly by supporting bone structures, thus leading to stable implants capable of bearing loads.

The problem was solved due to the surprising finding that the elementary body layers present a network-like structure and leave nearly ideal morphological spaces in their cavity system. These spaces are filled with a coating mass consisting of absorbable fillers (based on strong calcium compounds) and an absorbable binding substance. This induces bone ingrowth and the formation of a supporting bone arch.

SUMMARY OF THE INVENTION

Thus, the present invention provides a bone replacement material consisting of a three-dimensional supporting structure with elementary bodies or forming elements connected with one another and surrounding defined spaces. The elementary bodies are substantially spherical and have a size of at least 200 µm. The elementary bodies are held together such that each elementary body is held in rigid contact with at least three adjacent elementary bodies to define enclosed spaces therebetween which provide for bone ingrowth and penetration. A coating mass may be employed which, in turn, consists of absorbable fillers based on strong calcium compounds and an absorbable binding substance (matrix). Complete prostheses, anchoring parts for joint prostheses, coatings for bone and joint implants, bone dowels and closures for medullary cavities, all may be made of this type of bone replacement material.

The bone replacement material in accordance with the invention presents both a characteristic 3rd and 4th order structure. That is why not only bone ingrowth occurs in the interface; the formation of a supporting bone structure is also possible since the ingrowing trabeculae can grow together to form arches.

The formation of the 3rd order structure in the bone replacement material of the invention shall first be explained.

The surprising finding was the fact that samples consisting exclusively of layers of elementary bodies of a specific size and shape were completely penetrated by bone and that the bone structure in the section could hardly be distinguished from physiological spongiosa architecture.

Layered networks of spheres being 200 to 3,000 µm in size in particular were found to form intercorpuscular spaces which are filled with bone much more quickly than any other coating. In addition, the result is a nearly physiological and supporting 3rd order structure (trabecular architecture). The surface enlargement obtained in this way results in a huge surface capable of bearing forces. Said surface takes a nearly trajectorial course with respect to the resulting line of the forces acting on it.

Bone replacement material made exclusively of layered corpuscular networks and fully adapted to bone with respect to elasticity is completely penetrated by bone in a very short time (12 weeks), thus resulting in a permanent bone structure.

It was found that such an implant can bear bending load since it is distributed over the entire surface. Due to the huge surface area and the low mechanical load on the interface as a result, fatigue fractures no longer occur.

The bone replacement material of the invention has an additional advantage: The mass of the implant as a whole has been substantially reduced and thus, the primary top-heaviness of all prostheses now on the market has been eliminated. Said top heaviness can lead to a loosening of the prosthesis in the course of time.

Edge phenomena and stress concentration are avoided due to the preferably spherical structure of the elementary bodies. There is a uniform distribution of forces over the bone surface which is expressed by mature lamellar bone structures with a strict parallel fiber and layered arrangement.

Unlike a full stem prosthesis structured by individual spheres on its surface, the layered network structure of the spheres in the bone replacement material of the invention have a mechanically stimulating effect on the bone-building cell. This is shown by the fact that even the deep, ingrown bone structures present mature lamellar, i.e. capable of bearing biomechanical load, bone structures.

There is accelerated bone ingrowth especially when larger and smaller spheres are combined. A diameter ratio of 2:1 to 3:1 is particularly good. As an example, spheres with a diameter of between 200 and 1,000 µm (mean 500 µm) can be combined with spheres with a diameter of between 800 and 3,000 µm (mean 1,000 µm). The smaller spheres preferably have a diameter between 300 and 700 µm and more preferably between 450 and 550 µm, and the larger spheres a diameter of between 800 and 2,000 µm and more preferably between 900 and 1,200 µm. Both the smaller and the larger spheres each preferably present approximately the same diameter, e.g. 500 or 1,000 µm. Bone accumulation occurs more quickly around the smaller spherical elements, whereas the supporting bone arches are formed around the larger spherical elements. The fact that all of the spheres are rigidly connected to one another or at least in an adjustable and flexible connection to one another permits the formation of a nearly normal bone design. The permanent integration of the anchoring part is thus ensured with the vascular medullary spaces formed in between.

There is a relatively rigid connection when each of the spheres is in solid contact with at least three adjacent spheres. Depending on the supporting framework's structure, each sphere can be in solid contact with more than three, e.g. four, six or eight adjacent spheres, thus resulting in a rigid framework.

In the bone replacement material of the invention, the elementary bodies, preferably spheres, in the 3rd order structure are held together by threads made of absorbable organic polymers with a thickness of 50 to 300 µm and/or of non-absorbable threads or wires with a thickness of 100 to 750 µm, or they form three dimensional packs of maximum density (See FIG. 2).

The elementary bodies preferably consist of a metal such as titanium, tantalum, cobalt, chromium, molybdenum or one of their alloys, or of special steel and/or of ceramic or apatite or TCP (tricalcium phosphate) and/or a mixture of two or more of these materials and/or another inert material. The elementary bodies can preferably consist of an absorbable substance, e.g. a substance from which the 4th order structure is formed, such as a polypeptide, a polylactate, polyglycolate or one of their co-condensates, gelatine, collagen or a calcium compound as the matrix and preferably highly porous tricalcium phosphate or hydroxyl apatite particles or particles from a related calcium compound as fillers.

Even when the elementary bodies are not spherical, elementary bodies of two different sizes are preferably mixed; the above-mentioned diameters are each defined as mean diameters.

The spherical surfaces can be microstructured and the microstructures can take the form of spheres or spherical segments such as semi-spheres with a diameter of 15 to 30 µm.

In the bone replacement material of the invention, the spaces in the 3rd order elementary body structure are filled and/or their surface is covered with a coating mass. The special feature of this coating mass is the fact that it is completely absorbable (both the matrix and the fillers).

The microstructure of the spheres' surfaces (3rd order) together with the characteristic coating mass (if present) represent the 4th order structure (ultrastructure) of the bone replacement material of the invention.

This coating mass (4th order structure) will be explained in more detail in the following.

In one embodiment, the fillers consist of highly porous spherical particles with a diameter of 10 to 200 µm, preferably 15 to 50 µm, most preferably 15–30 µm and optimally approximately 20 µm. These spherical particles have a pore volume of 25–65%, more preferably greater than 40%. Due to the ultrastructure of the invention, the individual bone-building cell (osteoblast) and the osteoblast layer are stimulated to form specific trabeculae. Moreover, due to the structure of the bone replacement material of the invention, the individual bone cell is also stimulated. This causes very rapid bone ingrowth into the replacement material.

BRIEF DESCRIPTION OF THE DRAWINGS

The invention will be described in more detail on the basis of the following figures in which.

DETAILED DESCRIPTION OF THE PREFERRED EMBODIMENTS

Figure 1:
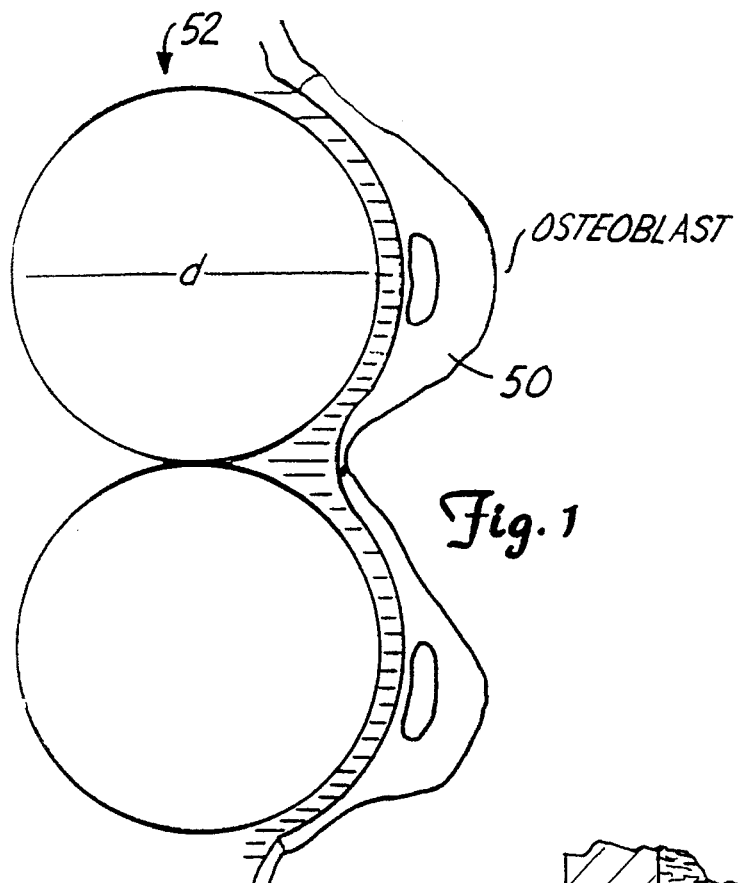
FIG. 1 is a 4th order structure spheres forming the base of an osteoblast.

Firmly anchored spheres 52 or spherical parts 15 to 50 µm in size, in particular 20 µm in size, have been found to represent the optimally structured surface (4th order ultrastructure) which an osteoblast 50 can recognize as its base; see FIG. 1. The spherical particle's diameter d is preferably approximately 20 μm and has the same magnitude as an osteoblast 50.

The pores of highly porous fillers can be filled with an absorbable and compatible substance. This substance is preferably the binder used. Specific examples of binders are: polypeptides, polylactates, polyglycolates or their co-condensates, gelatine, collagen and calcium compounds. The fillers are preferably harder than the binder.

An organic matrix was found to form an osteoblast layer much more quickly than a metal or ceramic surface. A ceramic surface was found to be better colonized than a metal surface. The surface of sintered apatite, however, undergoes even more rapid cell colonization than a ceramic surface. A collagen matrix was also found to be colonized (populated) more quickly by cells than a pure ceramic or a pure apatite surface. The best colonization rates are achieved when the organic matrix (e.g. collagen) contains tiny spheres of apatite. This coating mass is a preferred embodiment of the invention's 4th order structure (ultrastructure).

Figure 2:
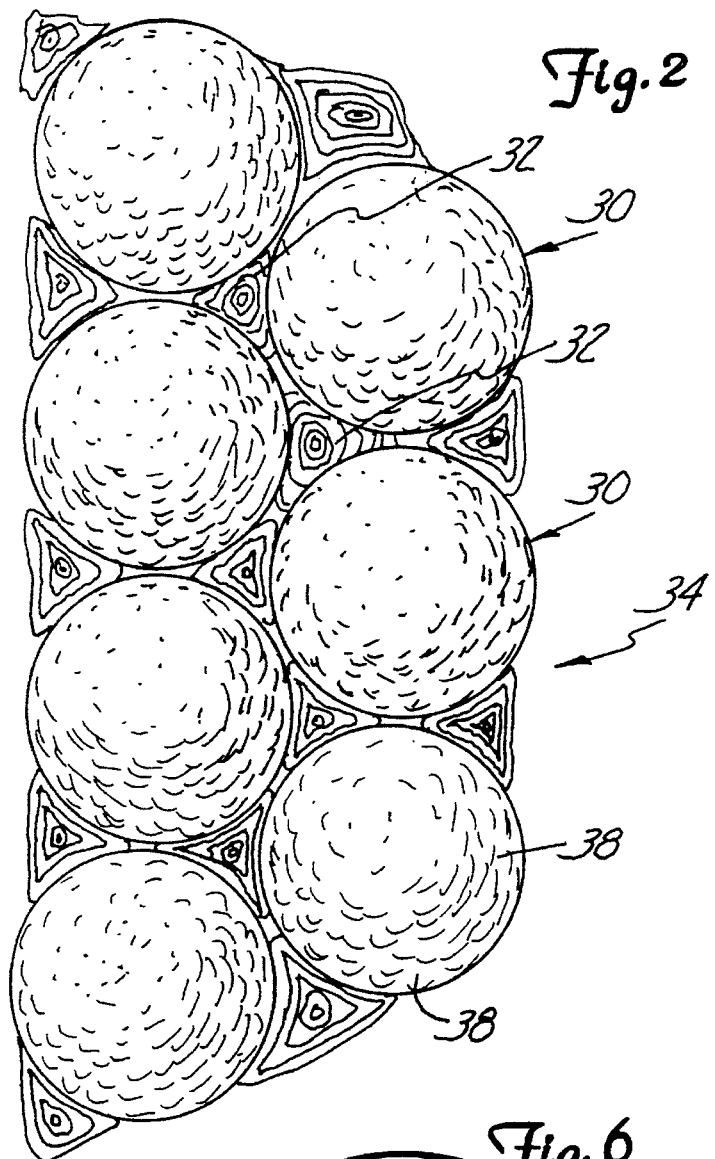
FIG. 2 is a schematic representation of a dense third order sphere pack with a 4th order spherical structure and indications of bone ingrowth.

The invention's coating mass 40 is completely absorbable. A completely absorbable matrix has great advantages compared to a nonabsorbable matrix. It is absorbed very quickly in the load-bearing zones and replaced by bone. A closed osteoblast layer 50 can be obtained in a very short time from a dense 3rd order sphere pack (see FIG. 2) together with a thin collagen coat which remains over the spheres 30. This osteoblast layer is capable of forming lamellar bone able to withstand heavy loads. Due to the density of the sphere pack and its concrete size, the primary arrangement of the bone-building cells has a specific structure; thus, a rearrangement of the cells and the trabeculae undergoing formation is not necessary. As a result, the absorption and new bone formation (remodelling) stages are not necessary.

In one embodiment of the bone replacement material, part of the coating mass's fillers take the form of fibers 43. The filamentous fillers preferably consist of fibers 43 of differing length with a thickness of between 100 and 300 μm, preferably approximately 200 μm. The fibers are preferably greater than 2 and up to 15 millimeters in length, most preferably at least 3 millimeters and at most 10 millimeters in length, the optimal length being between 4 and 5 millimeters.

Filamentous fillers 43 can consist of substances such as carbon collagen, polypeptides, polyacetates, polyglycolates or their co-condensates, gelatine or catgut. The share of filamentous fillers 43 can range from approximately 5 to 15%, preferably approximately 10%.

In a preferred embodiment of the invention, the filamentous fillers are part of a closed network sheathing the matrix.

Figure 5A:
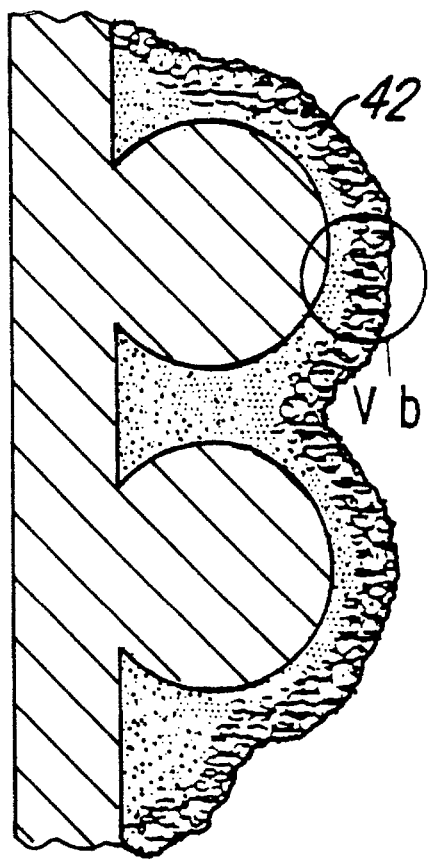
FIGS. 5a and 5b are views corresponding to FIG. 4 with bead chain-shaped fillers.
Figure 5B:
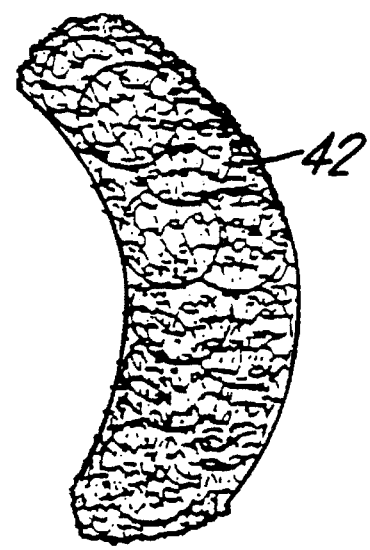

As illustrated in FIGS. 5a and 5b, a network structure can be made up of bead chains 42, the beads having a diameter of between 15 and 50 μm, preferably approximately 20 μm. The beads are so densely packed that they abut in a three-dimensional structure. The networks can be arranged as a stocking, in particular a multi-layered stocking.

Manufacturing the bone replacement material of the invention will be explained in the following using collagen as an example of a completely absorbable binder. Using conventional processes, a collagen mass is produced from animal bones. It can be mixed like a glue with spherical apatite or TCP. (In the invention, the expression 'apatite' preferably means 'hydroxyl apatite' and 'TCP' means 'tricalcium phosphate'). A dense pack of spheres is produced using infrasound, vibrators and/or other agitators. The supporting framework of elementary bodies is then impregnated with this coating mass. A structure is obtained in which the 3rd and 4th order structures of the invention are combined. This structure represents one of the invention's preferred bone replacement materials.

A 3rd order bone replacement material combined with the 4th order ultrastructure can also be obtained in the following manner: Spheres of an optimal size of between 200 and 3,000 μm are made from the collagen mass described above which contains apatite or TCP. These spheres are then placed on absorbable threads to form bead chains. Said chains are made into continuous stockings on a circular knitting machine. A bead chain network is formed.

Various forms of implants, e.g. for the treatment of bone deficiencies, can be produced by turning these bead chain structures in and out.

Figure 3:
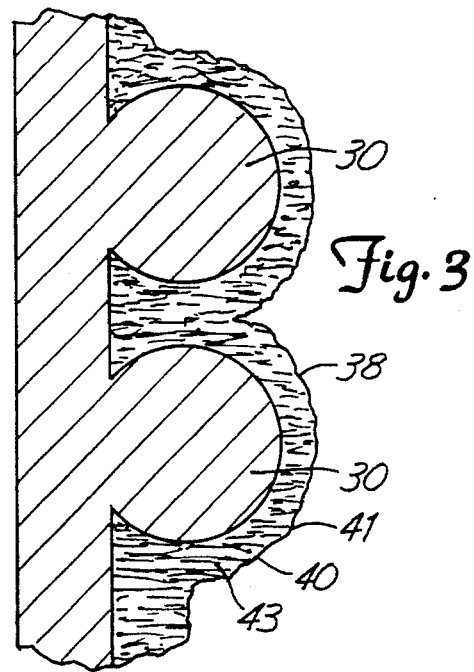
FIG. 3 is a schematic representation of two spherical elementary bodies with a coating mass with spherical fillers and fiber reinforced matrix.

The mechanical stability of the bone replacement material of the invention can be improved considerably by incorporating threads or fibers 36 of varying length or thread networks or thread webs into the matrix; see FIG. 3. Such bone replacement materials are also preferred embodiments.

Figure 4:
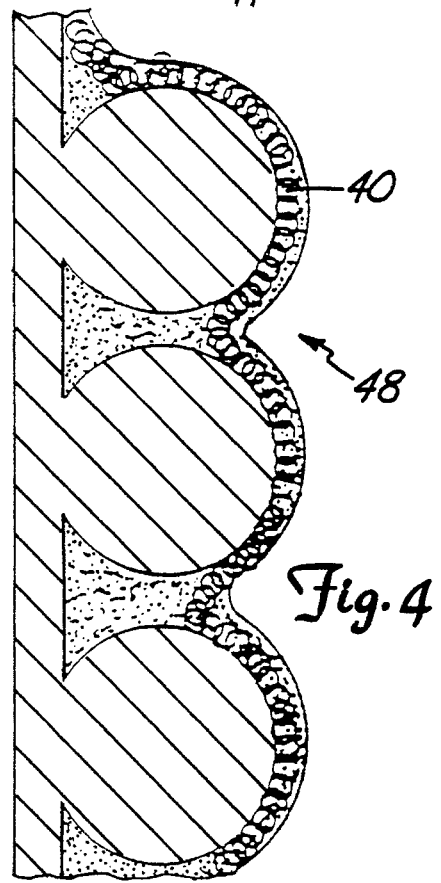
FIG. 4 is a view corresponding to FIG. 3 with stocking-shaped fillers impregnated through the matrix.

An especially preferred embodiment is the use of a knitted stocking or a network 48 in one or more layers as the filler. This is then impregnated with the binding substance. The laminations on the prostheses' anchoring parts which are obtained in this way are also preferred. These present very pronounced mechanical resistance; see FIG. 4.

Bone formation can be stimulated in a particularly effective way when the stockings take the shape of bead chains 42; see FIGS. 5a and 5b.

Such bead chains 42 can be obtained by incorporating tiny apatite spheres (15 to 30 μm, preferably 20 μm) in the threads when the latter are extruded. Such embodiments are also preferred. Multi-layered, three dimensional bead chain structures can also be used instead of the single-layered chain beads according to FIGS. 5a and 5b.

Figure 6:
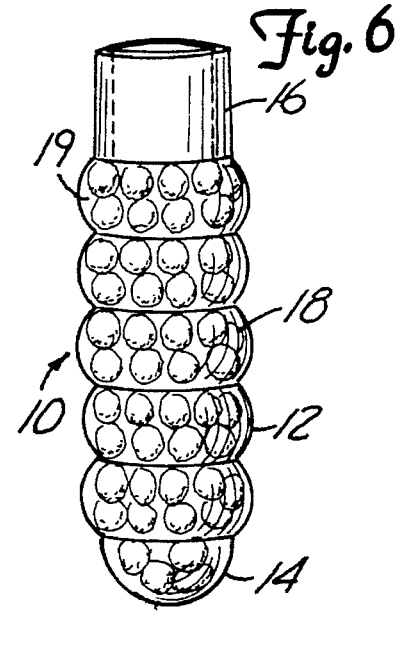
FIGS. 6 & 7 are a bone dowel and medullar cavity closures made of bone replacement material according to the invention.

FIG. 6 shows an example of a bone dowel 10 to anchor bone screws made of the bone replacement material of the invention. More specifically, the bone replacement material includes substantially spherical elementary bodies having a size of at least 200 μm and being together such that each elementary body is held in rigid contact with at least three adjacent elementary bodies to define enclosed spaces therebetween which provide for bone ingrowth and penetration, wherein the elementary bodies are provided and coated on the bone dowel. The bone dowel 10 has five rings or bulges 12, a nearly semi-spherical front end 14 and a cylindrical end section 16.

Spherical elementary bodies 18 form the matrix structure consisting of spheres which is sheathed by network 19. After being incorporated into bone, the dowel 10 sheathes and/or reinforces the bone.

The dowel is securely positioned in the surrounding bone and can provide a screw with long-term tensile strength when a screw is inserted into it. Anchoring in the bone is achieved by swelling the dowel or spreading it by screwing in a screw. The dowel can be provided with a number of longitudinal or transverse grooves to facilitate its insertion in bone, or it may consist of a double-walled stocking cage in accordance with the dowel presented in FIG. 6. The bead chains are held in this cage and connected with one another to form a supporting framework when the cage is turned.

Figure 7:
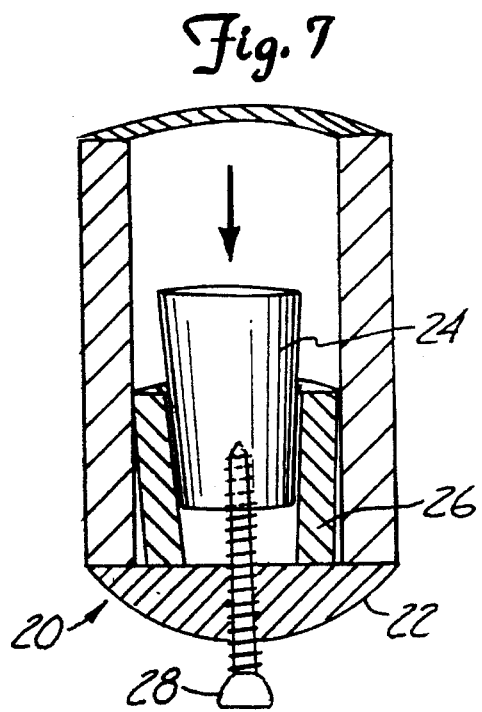

FIG. 7 shows a medullary cavity closure 20 made of the bone replacement material of the invention. More specifically, the bone replacement material includes substantially spherical elementary bodies having a size of at least 200 μm and being together such that each elementary body is held in rigid contact with at least three adjacent elementary bodies to define enclosed spaces therebetween which provide for bone ingrowth and penetration, wherein the elementary bodies are provided in the form of the medullary cavity closure and used to close the medullary cavity. The closure 20 presents a cap 22 over the medullary cavity stump, a cone-shaped plug 24 and a cone-shaped ring 26 into which the plug 24 is inserted by turning a screw 28. The ring 26 is then spread outwardly and is rigidly engaged in the interior of the honeycomb structure of the bone tubes schematically depicted in FIG. 7.

Closures made of the bone replacement material of the invention in the form of simple cylinders which swell in bone, or massive lamellar cylinders or screws are suitable means of treating bone gaps and filling holes in bone. They are inserted into the canal left by bone screws following their removal. Such closures create a hermetic seal against the internal pressure in the bone canals and/or medullary canals, prevent secondary hemorrhaging and the formation of hemotomae and accelerate bone healing.

Figure 8A:
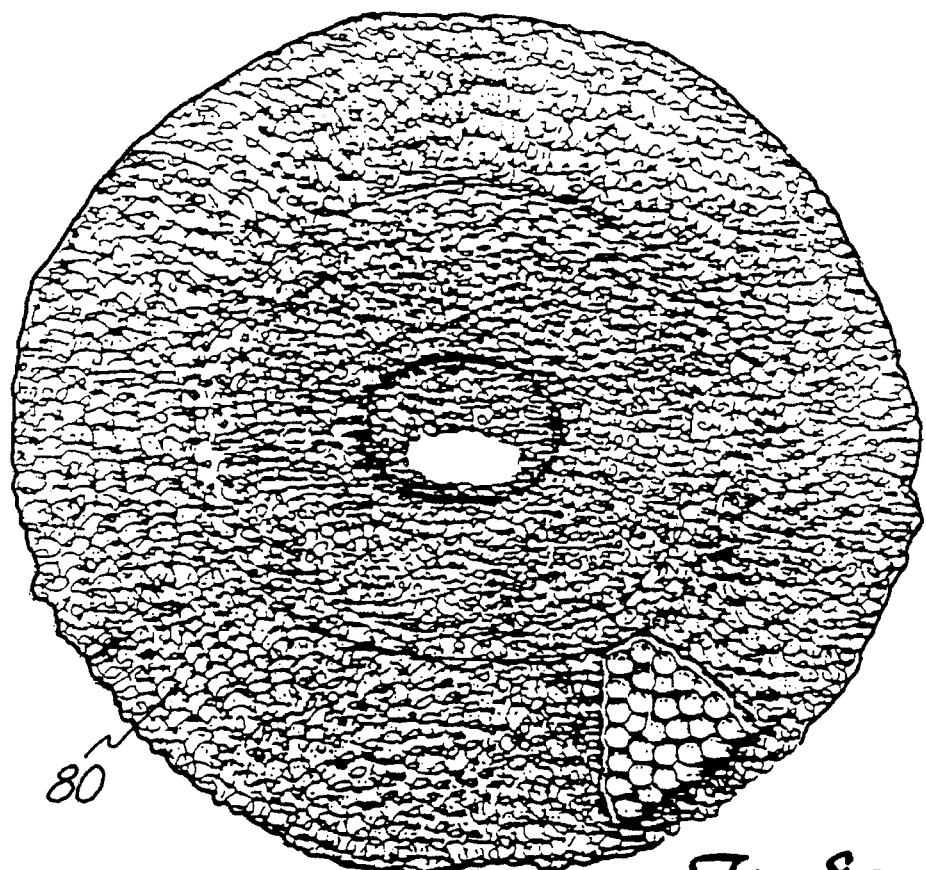
FIGS. 8–10 are further embodiments and uses of the material.
Figure 8B:
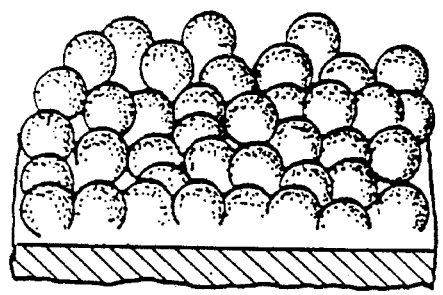
Figure 8C:
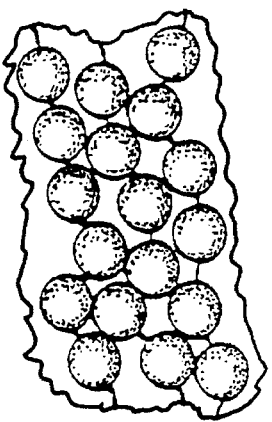

"Gap filling sponges" 80 (see FIG. 8a) in all shapes can be produced by turning these bead chain structures in and out. These are the familiar "scouring pad" shapes. They can be easily locked into bone gaps by spreading their "navel". They can be spread using a cone or peg-like stopper. FIG. 8b and 8c show a perspective diagram of a view on and a cross-section of one layer in the three-dimensional bead chain network.

The bone replacement material including substantially spherical elementary bodies having a size of at least 200 μm and held together such that each elementary body is held in rigid contact with at least three adjacent elementary bodies to define enclosed spaces therebetween which provide for bone ingrowth and penetration, can also be provided or coated on a prosthetic pin or stem to treat bone gaps. The coat shrinks while drying on the prosthesis' anchoring part, thus resulting in a closed contact between the supporting framework, the matrix coat, the fillers and the base material. A prosthesis coated in this way can be inserted in the bone without bone cement as a binder. With the appropriate support, closed bone-building layers are formed on the surface. They can give the prosthetic components a stable, bone support. Pronounced supporting trabeculae are formed, next to which the matrix coat is absorbed. The bone can then grow deep into the surface structure of the base body (supporting framework).

Figure 9A:
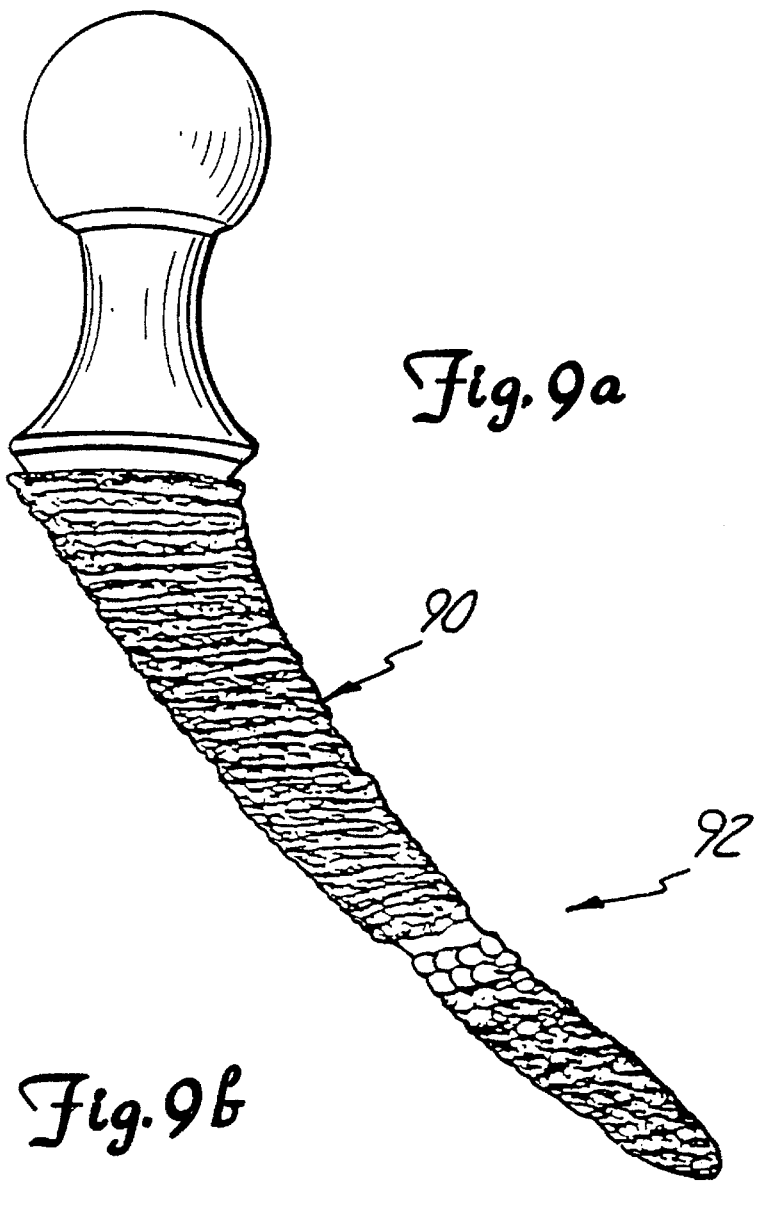
Figure 9B:
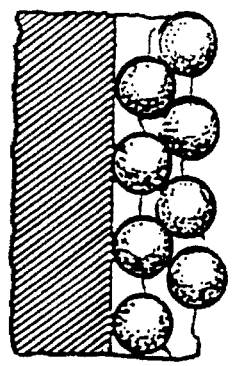
Figure 9C:
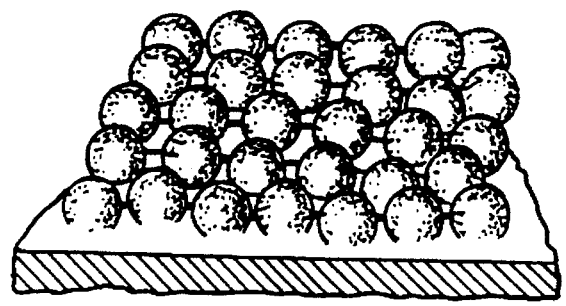

FIG. 9a shows the anchoring part 90 of a prosthesis 92 of the invention onto which the material of the invention has been applied. Said material consists of a bead chain structure. FIG. 9b shows a schematic cross-section of the base material and two layers of the three-dimensional structure. FIG. 9c shows a view on the uppermost layer in the structure.

The 3rd order structure can be both part of the prosthetic stem or part of the coat. If the absorbable coat consists of 3rd and 4th order shaping elements, the metal prosthetic stem must either have supporting ribs or continuous pores to permit bone ingrowth and bone underpinning.

Osteogenesis and bone ingrowth is much more rapid at the implant due to the inducing effect of the small apatite spheres coated, for example, with collagen than is the case in conventional coatings or non-coated implants.

In a special embodiment of the invention, the bone replacement material itself makes up the entire implant or the anchoring part of a prosthesis. The material is given the appropriate shape during production. The elementary bodies in the supporting framework can be a three-dimensional network strongly braced by inner or outer struts. The simplest form of implant would be sintered spheres. Such sphere packing can also be achieved by tying externally (retainer cage). Moreover, bead chains can be processed and braced, either by an inner, pressure-absorbing skeleton such as a supporting rib design or a "tire", or stiffened by means of individual weld points with adjustable elasticity. The stiffness and elasticity of certain parts of the bone replacement material can be set by the number and density of the weld points which can firmly connect the beads to one another.

Figure 10:
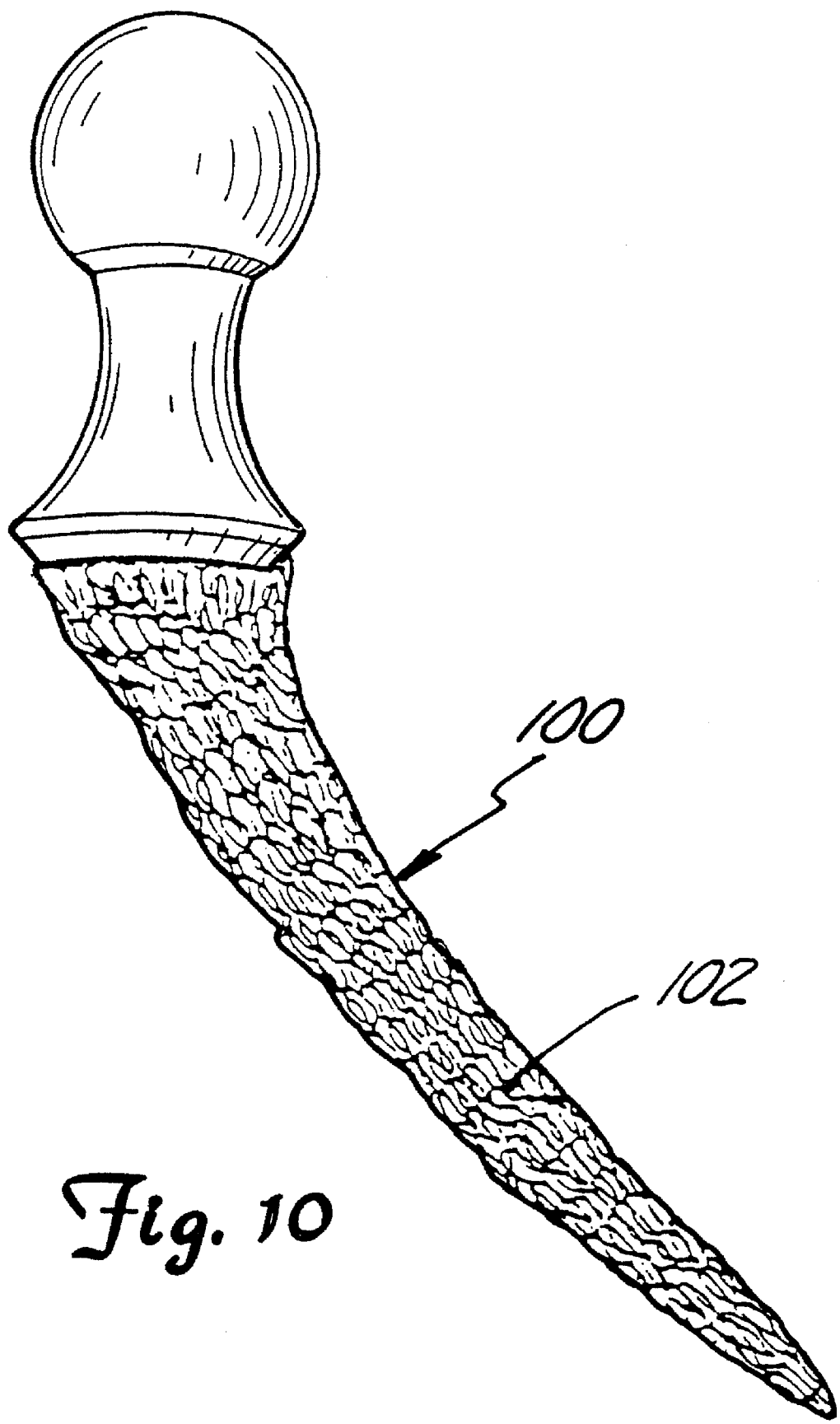

FIG. 10 shows an anchoring part 100 in which the network 102 can be both a sheath and—following the required stiffening or bracing—anchoring part. Artificial bones, for instance for tutorial purposes or for operation courses, can also be advantageously produced from the bone replacement material of the invention.

A three-dimensional network of the spherical elementary bodies can be turned or interlaced in such a way that implants with differing elasticities result (e.g. in different sections of the implant). The bone replacement material of the invention can take the form of a coat, a sheath, a cylinder, a flat coil spring, a sphere or a sponge.

The induced bone formation can be further increased by adding chemically active substances to the matrix substance. Chemotactically active substances from bone matrix and necrotic bone are known, for example, which contain "bone morphogenic proteins" and exert an especially great inducing effect on bone formation. Adding such admixtures is preferred.

Induced bone formation has been shown to be particularly favored when the highly porous spherical particles used as fillers are harder than the surrounding matrix. This allows them to exert a mechanically stimulating effect on the bone-building cell. Such an embodiment is also preferred.

An additional advantage of the bone replacement material of the invention is the fact that it contains a considerable amount of binding substance. This has been found to possess a great capacity with good release rates regarding the admixtures of active substances. Implants which have no access to the body's defense mechanisms due to a lack of vascularization are known to be at risk since they can easily be colonized by bacteria. This can be prevented by adding an antibiotic to the bone replacement material. A great deal of research his been conducted on such antibiotic admixtures in bone cements. To date, cement-free prostheses do not possess this protection. Bone replacement materials consisting of absorbable substances, however, make it possible to provide cement-free prostheses and implants of all kinds with an effective prophylactic protection against infection.

The local application of other medication, such as hemostatic agents, is known from external treatments. By admixing such substances to the bone replacement material of the invention, such substances can also take effect at organs not accessible to external treatment. Hemostatic agents in the binding substance provide an immediate hemorrhage control in the bone bed.

Vaso-active substances such as noradrenalin or one of its derivatives also provide hemorrhage control due to the vasoconstriction they cause. A soaking of the interface with blood is thus prevented and the mechanical strength of the interface is maintained for a longer period of time. As has already been mentioned, bone-inducing, chemotactically active substances can be admixed to the binding substance.

These cause new bone formation to set in more quickly. Hormone applications take a local effect with substances such as calcitonin. These prevent the newly formed bone from being resorbed.

The examples serve to clarify the invention.

EXAMPLE 1

A bone replacement material consisting of a three-dimensional supporting framework or elementary bodies in contact with one another and surrounding defined spaces, with or without a coating mass, can be produced as follows: The absorbable organic matrix substance polypeptide, e.g. polyglycolate or polylactate, together with the admixture of various additives as softeners, are heated in an extruder until they melt. The filler particles—highly porous tricalcium phosphate spheres—are then added and the entire mass is heated and stirred vigorously. The tricalcium phosphate spheres are preferably obtained from a highly porous sintered tricalcium phosphate, which for the most part presents a beta-whitlocked structure, by grinding in a ball mill.

In this way, a molten mass results with homogeneous filler distribution from stirring. Pressure is applied and the material in the molten mass is pressed out through fine nozzles and rolled in precipitation baths to threads with a thickness of approximately 200 µm. The spherical or spherical-like structures on the threads can be obtained in various ways. Spheres with a larger diameter, e.g. approximately 1,000 to 3,000 µm, can be threaded purely mechanically or the diameter of the infinitely variable nozzle opening can be changed by pulsation. The latter is the preferred method, in particular for spheres with a smaller diameter such as approximately 500 µm.

In this way, continuous bead chains can be obtained with an adjustable bead size by precipitating the molten mass in baths.

The smaller filler particles with a diameter of approximately 15–30 µm, possibly surrounded by matrix substance, may adhere on the outside to these bead chains.

The bead chains obtained in this way can then be knit to form continuous stockings on continuous round knitting machines produced, for example, by the Müller Co. in Weissenburg or the Dubied Co. in Neuenburg, Switzerland. By turning the stocking inwardly several times, a very dense, three-dimensional network of bead chains results. Its external shape resembles that of a tire. It can be ideally blocked in the bone cavity by means of a central spreader.

EXAMPLE 2

Layered corpuscular networks can also be formed by turning such networks outwardly. This is achieved by knitting or welding metal bead chains into networks, turning them outwardly in a few or several layers and stiffening them by welding. This makes it possible to set various elasticities over the entire implant. A very simple method consists of turning such networks over a core so that they completely enclose the core in a stocking-like manner. After turning the stocking 180°, for instance, a second layer can be turned. This process can be repeated until this continuous bead chain stocking possesses a multi-layered stratification.

A second process consists of welding and stiffening the framework of corpuscular layered networks according to a precisely calculated plan. An additional stiffening results from filling the cavity with an organic matrix substance, with or without filler particles presenting a 4th order structure. The matrix and filler particles are characterized by the fact that they are absorbable and can be coated with materials.

EXAMPLE 3

Individual or layered networks on complete prosthetic stems or anchoring parts consisting exclusively of layered corpuscular networks can be produced in various ways. Anchoring parts with up to two layers of corpuscular networks can be produced at reasonable costs using conventional methods. Producing the 3rd order structure is based on the process of casting into a lost form. This form is produced using layered networks of wax spheres as a meltable model. These processes are known from dentistry and are based on all simple surface structurings on cast metal shafts. The supporting framework obtained in this way is coated with an organic matrix if it is used to fill in cavities. The coating material preferably includes filler particles and exhibits all characteristics of the 4th order structure described above. Coating can be achieved by dipping the 3rd order structure into a molten mass of the 4th order structure.

EXAMPLE 4

The bone replacement material without a coating mass which consists of the three-dimensional supporting frame of the 3rd order structure of elementary bodies can also be used as a starting material for artificial bones. First of all the elementary bodies are poured into a casting composition, e.g. made of plastic, and are completely surrounded. The elementary bodies are then removed from the casting composition leaving only the bone-shaped structure of the casting composition. In this case the elementary bodies are made of a material which is chemically soluble in a solvent which does not affect the casting composition, or the elementary bodies are physically, e.g. electrolytically, removed from the casting composition.

I claim:

1. Bone replacement material comprising a three-dimensional supporting structure, the supporting structure comprising a plurality of elementary bodies, each elementary body being made of an absorbable substance and being substantially spherical, the size of the bodies being at least 200 µm, the elementary bodies being held together such that each elementary body is held in rigid contact with at least three adjacent elementary bodies to define enclosed spaces therebetween which provide for bone ingrowth and penetration.

2. Bone replacement material according to claim 1 wherein each elementary body is adjoined to each adjacent elementary body to form a three-dimensional pack of maximum density.

3. Bone replacement material according to claim 1 wherein said elementary bodies are made of a material selected from the group consisting of tricalcium phosphate, apatite, collagen and a polypeptide.

4. Bone replacement material according to claim 1 wherein the size of said substantially spherical elementary bodies is between 200 µm and 3,000 µm.

5. Bone replacement material according to claim 4 wherein the elementary bodies include a first set of elementary bodies having a diameter between 200 and 1,000 µm with a mean diameter of 500 µm and a second set of elementary bodies having a diameter between 800 and 3,000 µm with a mean diameter of 1,000 µm, the first set of elementary bodies being mixed with the second set of elementary bodies.

6. Bone replacement material according to claim 4 wherein a first set of elementary bodies with a diameter between 200 and 1,000 μm are mixed with a second set of elementary bodies with a diameter between 800 and 3,000 μm.

7. Bone replacement material according to claim 1 wherein said elementary bodies form a three-dimensional framework or network which is rigidly braced by struts.

8. Bone replacement material according to claim 1 wherein the material contains admixtures selected from the group consisting of hemostatic agents, bone-building substances, antibiotics, vasoactive substances and bone-active hormones.

9. Bone replacement material according to claim 8 further containing an antibiotic effective in the treatment of bone infections.

10. Bone replacement material according to claim 8 wherein the vaso-active substance is selected from the group consisting of noradrenalin and a noradrenalin derivative.

11. Bone replacement material according to claim 8 further containing calcitonin as the bone-active hormone.

12. Bone replacement material according to claim 1 wherein the material takes the form of a socket, a cylinder, a flat coil spring, a sphere or a sponge.

13. A method of replacing bone material comprising:

providing a bone replacement material comprising a three-dimensional supporting structure having a plurality of elementary bodies, said elementary bodies being made of an absorbable substance and being substantially spherical, the size of the bodies being at least 200 μm, the elementary bodies being held together such that each elementary body is held in rigid contact with at least three adjacent elementary bodies to define enclosed spaces which for provide bone ingrowth and penetration; and replacing bone material with the bone replacement material.

14. Bone replacement material according to claim 7 wherein the elementary bodies of the three-dimensional network are interlaced.

15. A method of coating a bone or joint implant to treat bone gaps, said method comprising:

providing a bone replacement material comprising a three-dimensional supporting structure having elementary bodies, said elementary bodies being made of an absorbable substance, being substantially spherical, and being held together so that elementary body is held in rigid contact with at least three adjacent elementary bodies to define enclosed spaces which provide for bone ingrowth and penetration; and coating the bone or joint implant with the bone replacement material.

16. A method of replacing a joint comprising:

providing a bone replacement material in the form of a prosthesis, the bone replacement material comprising a three-dimensional supporting structure having elementary bodies, said elementary bodies being made of an absorbable substance, being substantially spherical, and being held together so that each elementary body is held in rigid contact with at least three adjacent elementary bodies to define enclosed spaces which provide for bone ingrowth and penetration; and replacing the joint with the bone replacement material.

17. A method of anchoring bone screws using a bone dowel comprising:

providing a bone replacement material in the form of a bone dowel, the bone replacement material comprising a three-dimensional supporting structure having elementary bodies, said elementary bodies being made of an absorbable substance, being substantially spherical, and being held together so that each elementary body is held in rigid contact with at least three adjacent elementary bodies to define enclosed spaces which provide for bone ingrowth and penetration; and anchoring bone screws using the bone dowel.

18. A method of closing off medullary cavities comprising:

providing a bone replacement material in the form of a medullary cavity closure comprising a three-dimensional supporting structure having elementary bodies, said elementary bodies being made of an absorbable substance, being substantially spherical, and being held together so that each elementary body is held in rigid contact with at least three adjacent elementary bodies to define enclosed spaces which provide for bone ingrowth and penetration; and closing the medullary cavity using the bone replacement material.

* * * * *